United States Patent
Peterman et al.

(10) Patent No.: US 12,370,060 B2
(45) Date of Patent: Jul. 29, 2025

(54) METHODS AND DEVICES FOR ALTERING SPINAL LORDOSIS AND/OR KYPHOSIS DURING SPINAL FUSION

(71) Applicant: 3SPINE, INC, Chattanooga, TN (US)

(72) Inventors: Marc M Peterman, Duxbury, MA (US); Steven C Humphreys, Chattanooga, TN (US); Scott Hodges, Soldatna, AK (US)

(73) Assignee: 3SPINE, Inc., Chattanooga, TN (US)

( * ) Notice: Subject to any disclaimer, the term of this patent is extended or adjusted under 35 U.S.C. 154(b) by 169 days.

(21) Appl. No.: 18/236,924

(22) Filed: Aug. 22, 2023

(65) Prior Publication Data

US 2023/0390076 A1  Dec. 7, 2023

Related U.S. Application Data

(60) Division of application No. 17/023,864, filed on Sep. 17, 2020, now Pat. No. 11,890,202, which is a continuation of application No. 15/955,611, filed on Apr. 17, 2018, now Pat. No. 10,821,003.

(60) Provisional application No. 62/486,329, filed on Apr. 17, 2017, provisional application No. 62/654,963, filed on Apr. 9, 2018.

(51) Int. Cl.
*A61F 2/44* (2006.01)
*A61B 17/70* (2006.01)
*A61F 2/30* (2006.01)

(52) U.S. Cl.
CPC ............ *A61F 2/447* (2013.01); *A61F 2/4405* (2013.01); *A61F 2/442* (2013.01); *A61F 2/4425* (2013.01); *A61B 17/7001* (2013.01); *A61F 2002/30331* (2013.01); *A61F 2002/30563* (2013.01); *A61F 2002/30578* (2013.01); *A61F 2002/30624* (2013.01); *A61F 2002/30652* (2013.01); *A61F 2002/30654* (2013.01); *A61F 2002/30662* (2013.01); *A61F 2002/30884* (2013.01); *A61F 2002/448* (2013.01); *A61F 2220/0033* (2013.01); *A61F 2250/0004* (2013.01); *A61F 2310/00796* (2013.01); *A61F 2310/00976* (2013.01)

(58) Field of Classification Search
CPC .......... A61F 2/44; A61F 2/442; A61F 2/4455; A61F 2/447
See application file for complete search history.

(56) References Cited

U.S. PATENT DOCUMENTS

| | | | | |
|---|---|---|---|---|
| 8,070,815 B2* | 12/2011 | Yu | | A61F 2/4425 623/17.14 |
| 8,075,596 B2* | 12/2011 | Molz | | A61F 2/4405 606/257 |
| 8,864,832 B2* | 10/2014 | Carls | | A61F 2/4405 623/17.16 |
| 9,770,338 B2* | 9/2017 | Carls | | A61F 2/4425 |
| 2002/0068941 A1* | 6/2002 | Hanson | | A61F 2/4611 606/79 |
| 2004/0152970 A1* | 8/2004 | Hunter | | A61B 34/20 600/424 |

(Continued)

*Primary Examiner* — Ellen C Hammond
(74) *Attorney, Agent, or Firm* — BRAINSPARK ASSOCIATES, LLC

(57) ABSTRACT

Disclosed are systems, devices, methods and surgical procedures for altering and/or correcting the alignment of adjacent bones, including bones of the spine, during spinal fusion or similar procedures.

20 Claims, 18 Drawing Sheets

(56) References Cited

U.S. PATENT DOCUMENTS

| | | | |
|---|---|---|---|
| 2005/0154461 A1* | 7/2005 | Humphreys | A61F 2/4425 623/17.11 |
| 2006/0241769 A1* | 10/2006 | Gordon | A61B 17/7041 606/279 |
| 2006/0247654 A1* | 11/2006 | Berry | A61B 17/1757 606/96 |
| 2008/0027547 A1* | 1/2008 | Yu | A61F 2/4425 623/17.13 |
| 2009/0299478 A1* | 12/2009 | Carls | A61F 2/4425 623/17.16 |
| 2018/0008426 A1* | 1/2018 | Carls | A61F 2/442 |
| 2018/0228619 A1* | 8/2018 | Peterman | A61F 2/4405 |

* cited by examiner

 
FIG. 15B     FIG. 15A
 
FIG. 16B     FIG. 16A
FIG. 16C
      
FIG. 17A     FIG. 17B     FIG. 17C
   
FIG. 17D     FIG. 17E

METHODS AND DEVICES FOR ALTERING SPINAL LORDOSIS AND/OR KYPHOSIS DURING SPINAL FUSION

CROSS-REFERENCE TO RELATED APPLICATIONS

This application is a continuation application of U.S. application Ser. No. 17/023,864, filed on Sep. 17, 2020, which is a continuation of, and claims priority to, U.S. application Ser. No. 15/955,611, filed on Apr. 17, 2018 and issued as U.S. Pat. No. 10,821,003 on Nov. 3, 2020, which in turn claims the benefit of and priority to U.S. Provisional Patent Application Ser. No. 62/654,963 entitled "Spinal Osteotomy," filed Apr. 9, 2018, and U.S. Provisional Patent Application Ser. No. 62/486,329 entitled "HHALL Osteotomy," filed Apr. 17, 2017. The disclosures of each of these references are incorporated by reference herein in their entireties.

TECHNICAL FIELD

The present invention relates generally to devices, methods, systems and techniques for repairing and/or stabilizing the spine and/or other bones of a patient during spinal surgery.

BACKGROUND

At times, the source of a patient's back pain may not be clear. Among possible causes for such pain are disease, degradation and/or injury to the spinal bones and/or discs of the spine, as well as to various ancillary structures such as the lamina and/or associated facet joints. While spinal fusion and/or disc arthroplasty procedures have been successful in treating spinal joints to reduce pain, such treatments are often limited in their efficacy, often fuse or immobilize portions or a patient's spine, and are often unable to address and/or correct severe spinal deformities, including spinal dislocations and/or curvature abnormalities such as juvenile and/or adult scoliosis. Therefore, a motion preserving joint replacement system is needed that can reduce and/or correct severe spinal deformities while replacing all or part of the function of the spinal disc and/or associated spinal structures.

SUMMARY OF THE INVENTION

In various embodiments, surgical methods and techniques are described wherein portions of a patient's spinal bones may be shaped, shaved, resected and/or removed, including portions of a vertebral endplate and/or pedicular portion(s) (and/or associated structures), with at least one or more portions of the pedicle retained to provide at least partial support for a prosthetic system that is implanted between the upper and lower vertebrae.

In various embodiments, the prosthetic system can comprise an upper joint component and a lower joint component. The upper joint component can comprise an upper contact surface and an upper articulation surface, and the lower joint component can comprise a lower contact surface and a lower articulation surface configured to movably engage the upper articulation surface to form an articulating joint. The articulating joint is adapted for implantation within a disc space between the upper and lower vertebrae, allowing the upper and lower vertebrae to move relative to one another. The lower joint component will also desirably include a support or bridge component extending posteriorly from the disc space, with at least a portion of the bridge component including an outer surface which abuts and/or engages with at least a portion of a pedicle and/or portions of the vertebral arch.

In another embodiment, a prosthetic system for implantation between upper and lower vertebrae comprises an upper joint component having an upper contact surface and an upper articulation surface. The system further has a lower joint component comprising a lower contact surface and a lower articulation surface configured to movably engage the upper articulation surface to form an articulating joint. The articulating joint is configured for implantation within a disc space between the upper and lower vertebrae, allowing the upper and lower vertebrae to move relative to one another. The lower joint component can further include a posterior support which extends from a posterior aspect of the lower joint component, the posterior support including at least one fixation element for securing the lower joint component to the lower vertebrae.

In still another embodiment, a surgical method comprises non-invasively imaging at least upper and lower vertebral bodies of a patient's spine, and then preoperatively planning the surgical removal of some portions of an endplate and one or more pedicles of the lower vertebral body to alter, restore and/or correct the alignment between the upper and lower vertebral bodies to a desired and/or more anatomically correct alignment. Surgical removal according to the preoperative plan can be accomplished, which can include removal of the endplate and/or a portion of one or more pedicles of the lower vertebral body, and then insertion of a prosthetic system between the upper and lower vertebrae, wherein the system comprises an upper joint component and a lower joint component, with the lower joint component including a support extending posteriorly from the lower joint component, the posterior support including a surface adapted and configured to fit within at least a remaining portion of one or more pedicles of the lower vertebral body.

In the various embodiments described herein the planning and surgical corrections to the spinal alignment can include alterations to the lordotic curvature of the patient's spine, alterations to the lateral curvature of the patient's spine (i.e., to address scoliosis, for example), and/or various combinations thereof. If desired, a surgical correction to a specific region of the spine may result in a more-normal anatomical alignment of the affected segment, or the surgical correction may result in an alignment that is further away from the natural alignment (such as where the treated segment desirably compensates for other misaligned levels that may not be surgically treated). In various embodiments, the anatomical imaging, analysis, approach, vertebral preparation, implant preparation and/or placement can be accomplished with the aid of surgical navigation and/or robotic guidance. Due to the complex nature of the preoperative planning and/or execution, these tools may be particularly well suited for the present invention to allow execution of the plan in the operative environment.

BRIEF DESCRIPTION OF THE DRAWINGS

The foregoing and other objects, aspects, uses, features, and advantages of embodiments will become more apparent and may be better understood by referring to the following detailed description of the preferred embodiments, taken in conjunction with the accompanying drawings, wherein:

FIGS. 15A through 16C depict exemplary surgical rasps for preparing vertebral anatomy;

FIGS. 17A through 17E depict cross-sectional views of exemplary rasps and alignment tools for use in preparing spinal anatomy;

DETAILED DESCRIPTION

Figure 1:
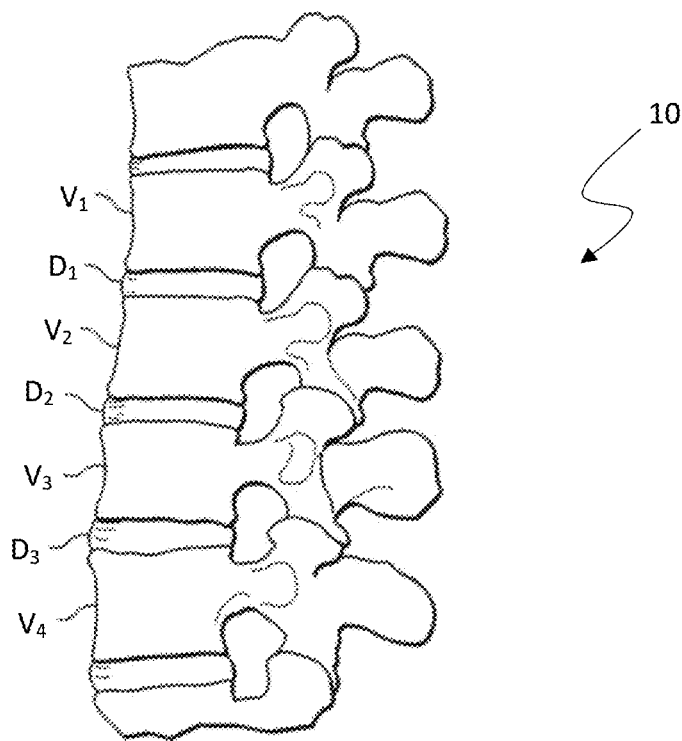
FIG. 1 depicts a sagittal view of the lumbar spinal region of a healthy, human spinal column.

Various features of the present invention include the recognition of a need for a more effective and versatile system of addressing spinal disease and deformities, including the correction and/or alteration of spinal levels using a motion preserving construct. A variety of configurations, sizes and shapes of such components and associated tools can be utilized in diverse anatomical regions, including use in spinal surgery as well as other anatomical locations. In various medical applications, the disclosed components and related surgical tools and techniques can desirably facilitate the treatment of various types of bone disease and/or damage by surgeons, which can be important to achieve the most accurate and best implant performance and/or fit, as well as facilitate patient recovery.

This specification describes novel systems, devices and methods to treat spinal fractures. Aspects of the present invention will be described with regard to the treatment of vertebral bodies at the lumbar and/or thoracic levels. It should be appreciated, however, that various aspects of the present invention may not limited in their application to thoracic or lumbar injuries. The systems and methods may be applicable to the treatment of fractures in diverse bone types. Embodiments will now be described with reference to the drawings, wherein like reference numerals are used to refer to like elements throughout. It should be understood that the figures are not necessarily to scale.

The present disclosure relates generally to systems and methods for spinal surgery and, more particularly in some embodiments, to spinal arthroplasty systems and methods for posterior implantation. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring first to FIG. 1, a sagittal view of a vertebral column 10 is shown, illustrating a sequence of vertebrae V1, V2, V3, V4 separated by natural intervertebral discs D1, D2, D3, respectively. Although the illustration generally depicts a lumbar section of a spinal column, it is understood that the devices, systems, and methods of this disclosure may also be applied to all regions of the vertebral column, including thoracic and cervical regions.

Figure 2:
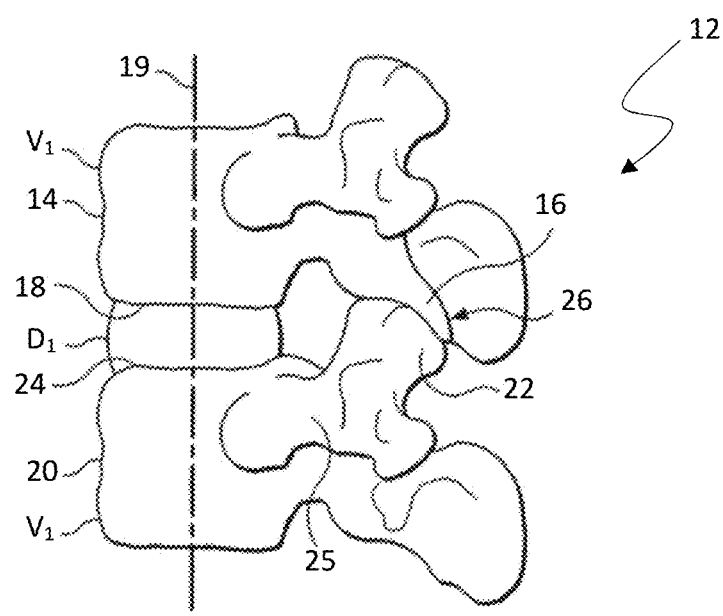
FIG. 2 depicts a sagittal view of a single spinal joint.

Referring now to FIG. 2, a vertebral joint 12 of the vertebral column 10 includes the adjacent vertebrae V1, V2 between which the intervertebral disc D1 extends. The vertebra V1 includes a generally cylindrical vertebral body portion 14, an inferior articular process 16, and an inferior endplate 18. The vertebra V2 includes a generally cylindrical vertebral body portion 20, a superior articular process 22, and a superior endplate 24. For reference purposes, a longitudinal axis 19 extends through the centers of the cylindrical vertebral body portions 14, 20. A pedicle 25 extends between the vertebral body portion 20 and superior articular process 22. The inferior articular process 16 and the superior articular process 22 form a facet or zygapophyseal joint 26. The facet joint 26 has a fluid filled capsule and cartilage to provide articulating surfaces for the articular processes 16, 22. Both the disc D1 and the facet joint 26 permit motion between adjacent bone surfaces, allowing the total vertebral joint 12 a normal range of flexion/extension, lateral bending, and rotational motion. As the disc D1 and/or the facet joint 26 deteriorate due to aging, injury, disease, or other factors, all or portions of the disc, the facet joint, and/or the articular processes 16, 22 may be removed and replaced by a prosthetic device which may preserve motion in the spinal joint 12. Although not described in detail, a second bilateral prosthetic device may also be used to replace a portion of the function of disc D1 and/or the function of a second facet joint opposite the facet joint 26.

Figure 3A:
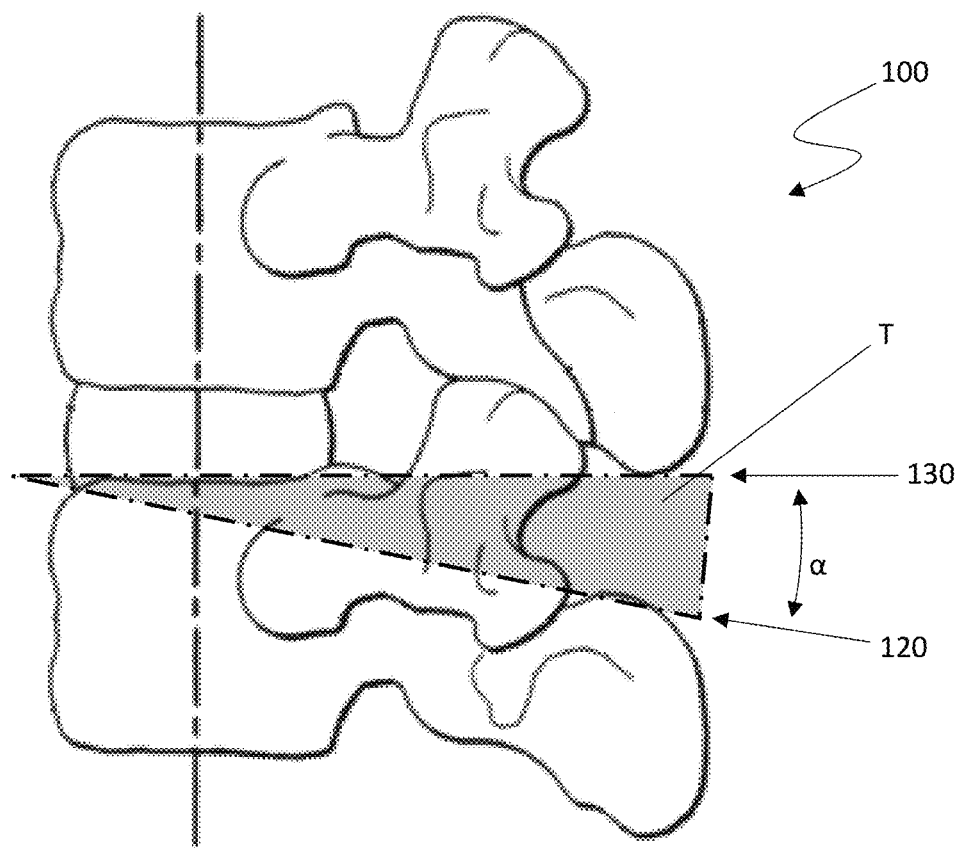
FIG. 3A is lateral view of one exemplary embodiment of a surgical technique for altering the alignment of a functional spinal unit.

FIG. 3A depicts a side view of one exemplary spinal motion unit 100 that is undergoing a surgical procedure in accordance with one exemplary embodiment of the present invention. In this embodiment, preoperative image data of the spinal motion unit has been obtained, and a surgical plan to alter the alignment of the spinal motion has being proposed. In this embodiment, a proposed lower component alignment path 120 has been presented, which will desirably result in the surgical removal of a "wedge" of bony material from the lower vertebral body 105 and/or one or both pedicles 110, which is represented by the shaded triangle "T" of FIG. 3A (involving removal of bony material at or below the anatomical alignment line 130 up to the revised alignment line of 120). Desirably, this surgical plan will allow some and/or all of at least the bottom of the pedicles to be preserved during such removal, such that the remaining portions of the pedicle are attached to the vertebral body, to provide additional stability to lower surfaces of the implant.

If desired, the resection may be symmetrical on each side of the vertebral body, or the resection may be asymmetrical in some fashion.

In various embodiments, the use of robotics and/or computer guided surgical platforms (and/or computer-aided navigation) are contemplated herein, including in the planning and/or execution stages of the surgery.

Figure 3B:
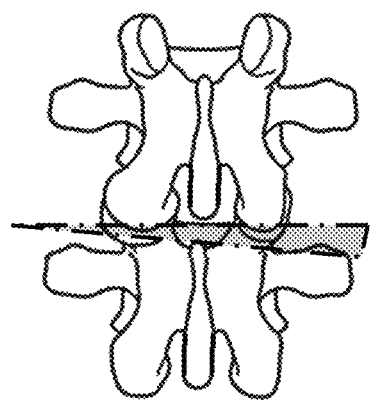
FIG. 3B is a posterior view of another exemplary embodiment of a surgical technique for altering the alignment of a functional spinal unit.

FIG. 3B depicts a posterior view of the exemplary spinal motion unit 100, where an asymmetrical resection is being planned to desirably correct an undesirable medial/lateral curvature of the spine. In this embodiment, more material will be resected from right side of the spinal motion unit than from the left side, which will desirably induce a slight medial curvature to the patient's spine (i.e., providing a desired coronal plan correction). In addition, as previously noted, the surgical plan will desirably allow some and/or all of at least the bottom of the pedicles to be preserved during such removal, such that the remaining portions of the pedicle are attached to the vertebral body, to provide additional stability to lower surfaces of the implant.

Figure 3C:
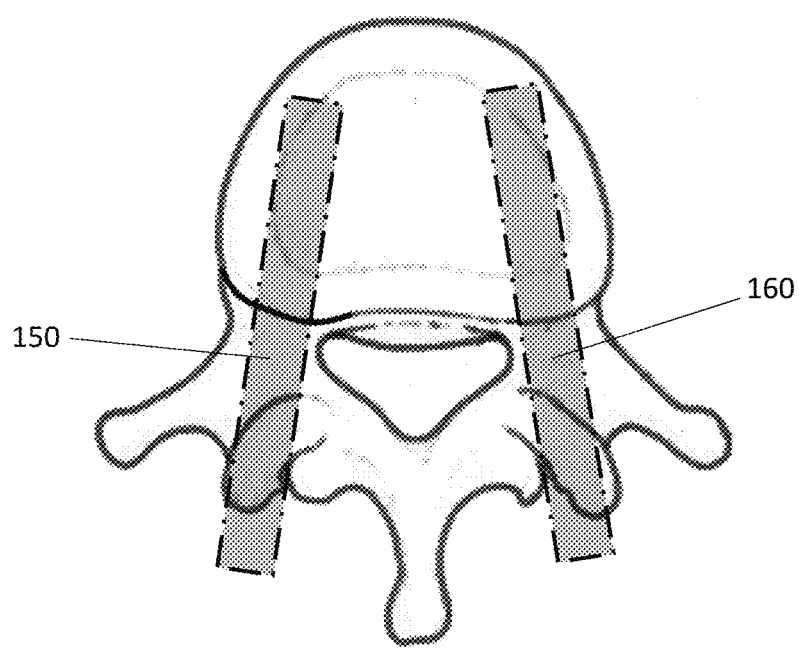
FIG. 3C is a superior view of a surgical technique for altering the alignment of a functional spinal unit.

FIG. 3C depicts a top view of a vertebral body of the surgical plan on FIG. 3A, in which the proposed bone "wedges" are shown in shadow as planning boxes 150 and 160. In this embodiment, the wedges could be taken from both sides for sagittal correction, or both side asymmetrically or unilaterally for combined coronal and sagittal correction.

Figure 4A:
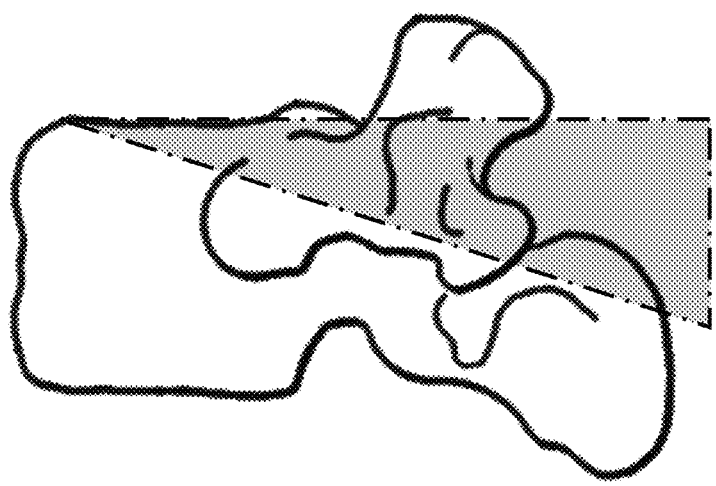
FIGS. 4A through 4D depicts exemplary planning steps for altering and/or correcting the lordotic alignment of a functional spinal unit.
Figure 4B:
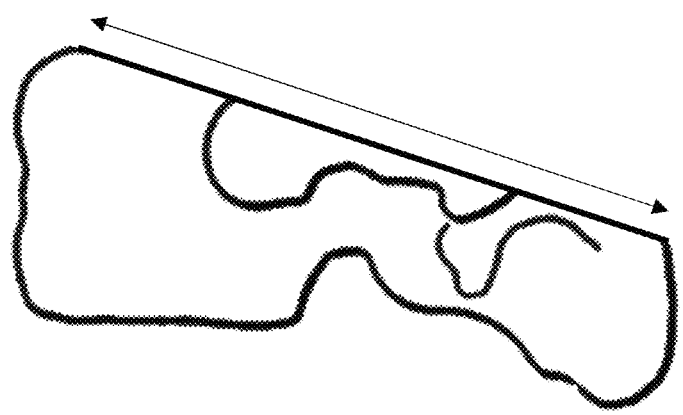
Figure 4C:
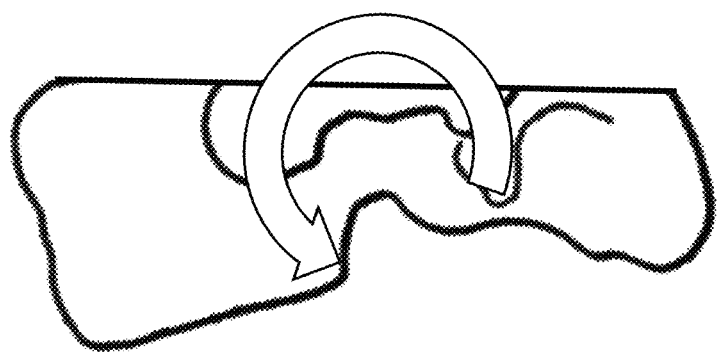
Figure 4D:
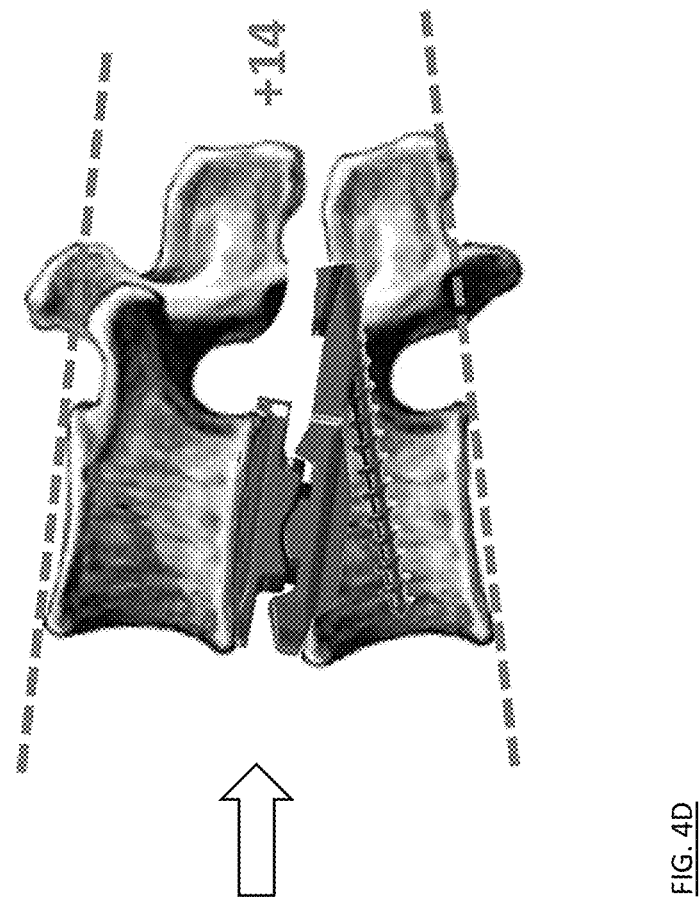
Figure 4D:
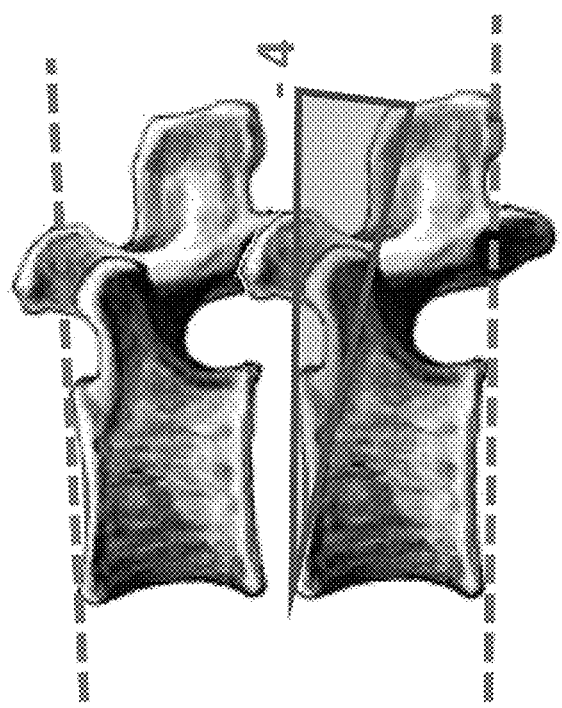
Figure 5:
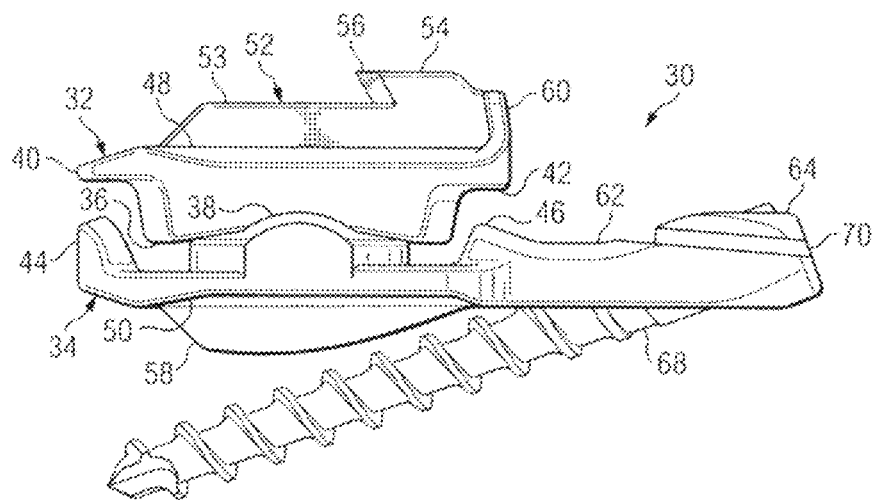
FIGS. 5 through 9 depict one exemplary embodiment of a prosthetic device which allows for significant resection of a vertebral body and/or pedicle and associated spinal structures, while preserving spinal stability and motion.
Figure 6:
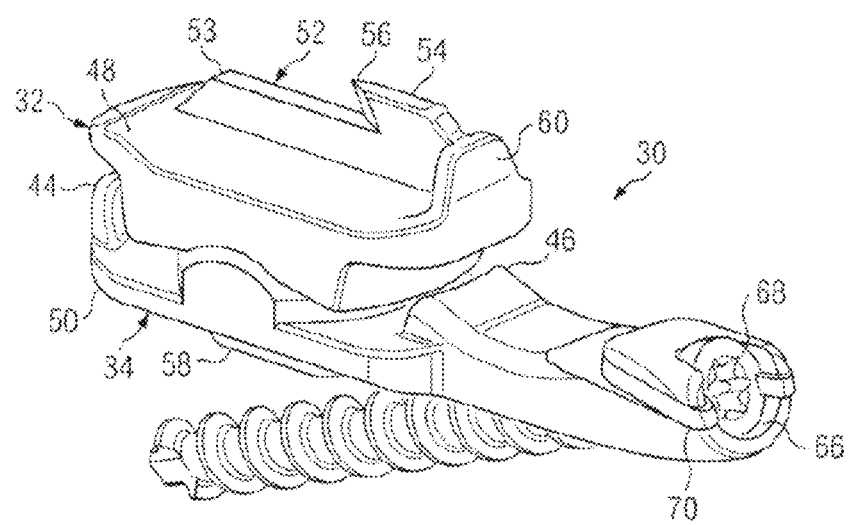
Figure 7:
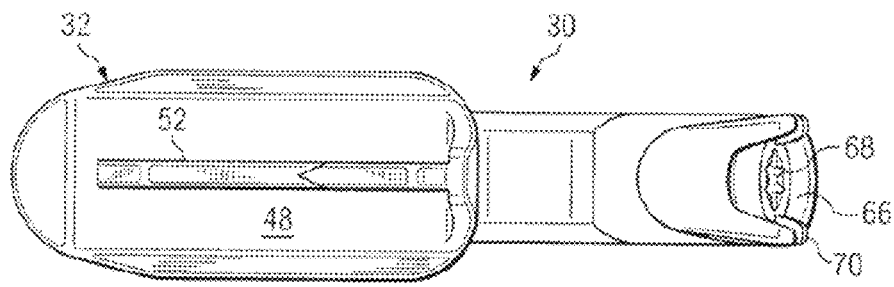
Figure 8:
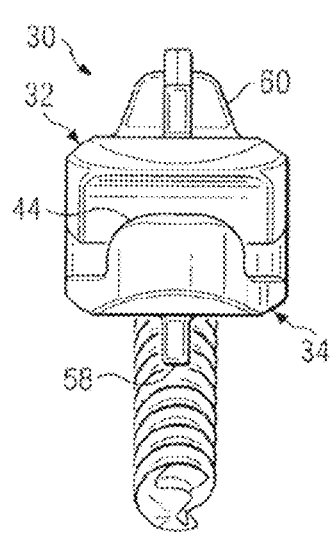
Figure 9:
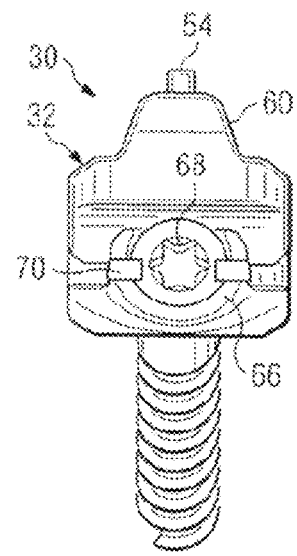
Figure 10:
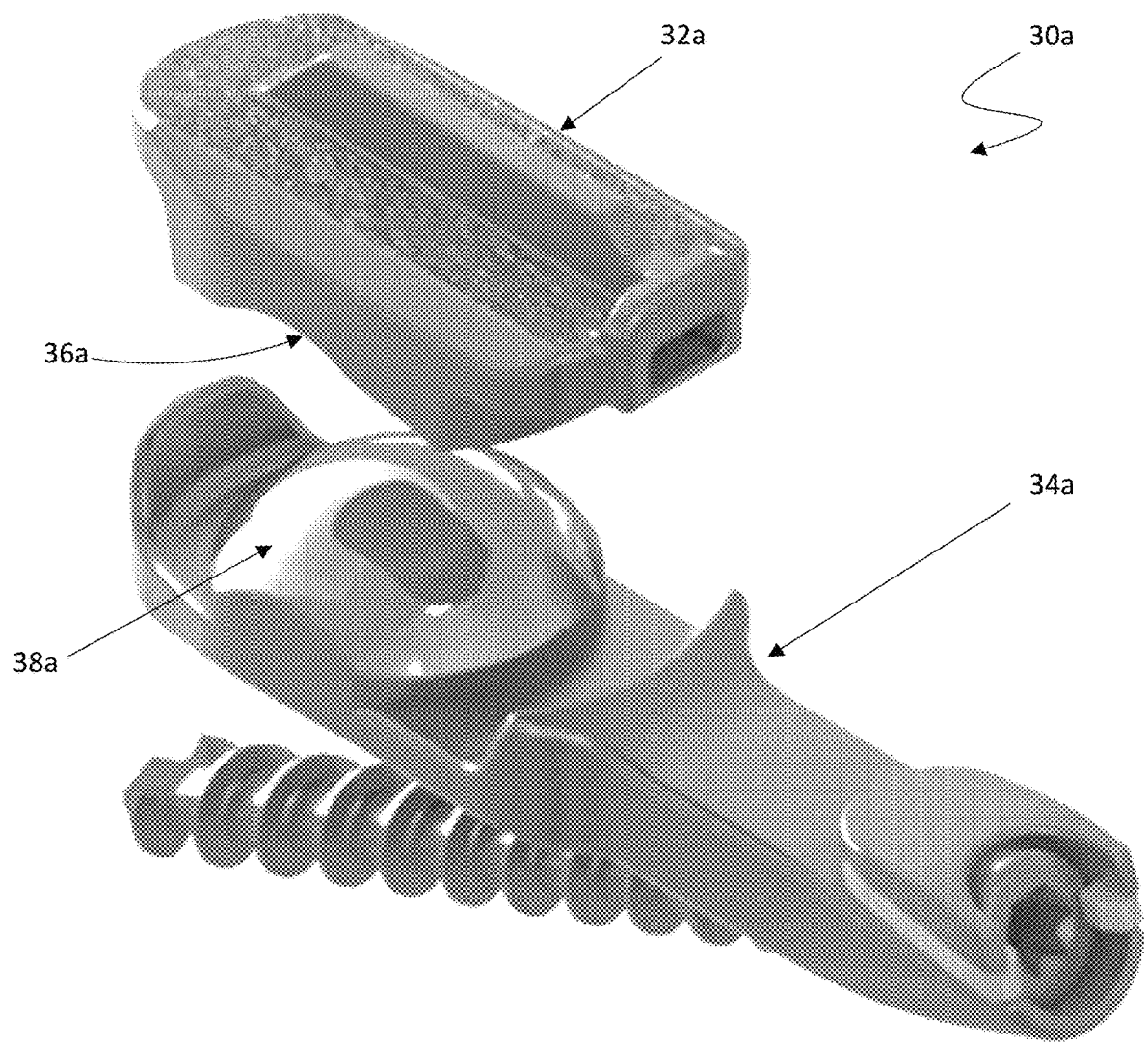
FIGS. 10 through 14 depict another exemplary embodiment of a prosthetic device which allows for significant resection of a vertebral body and/or pedicle and associated spinal structures.
Figure 11:
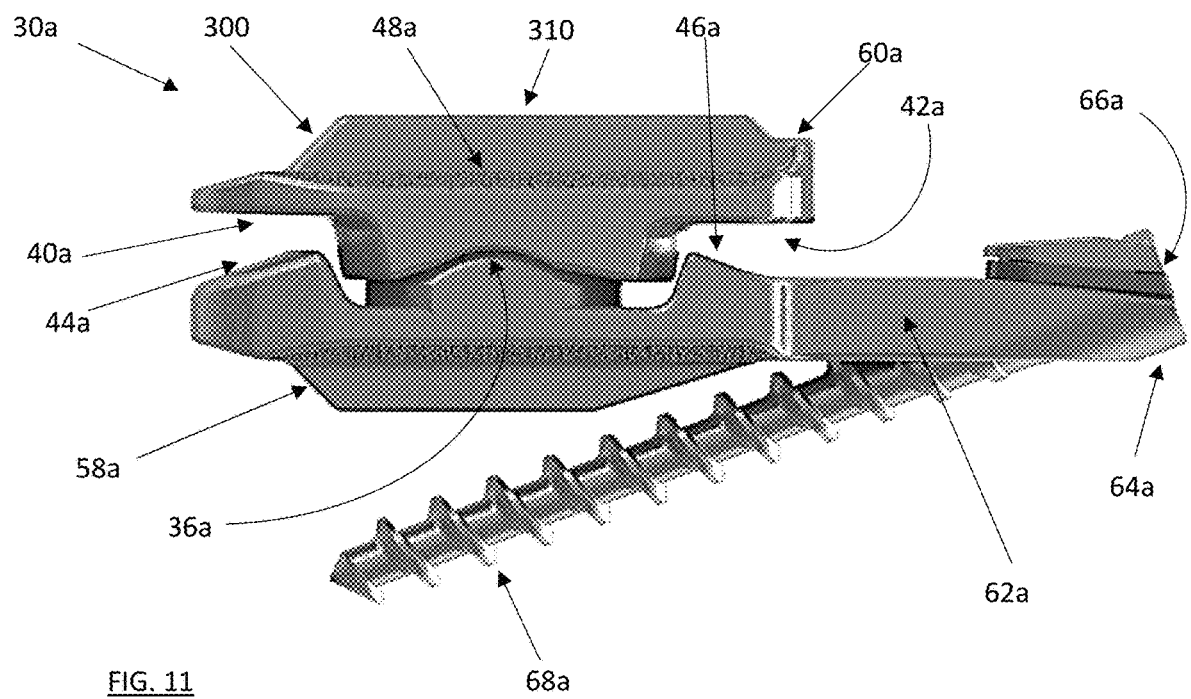
Figure 12:
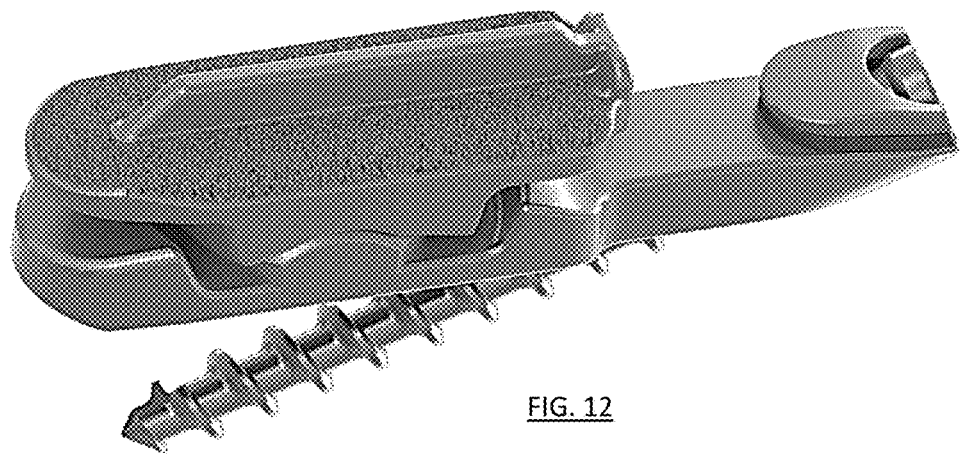
Figure 13:
Figure 14:
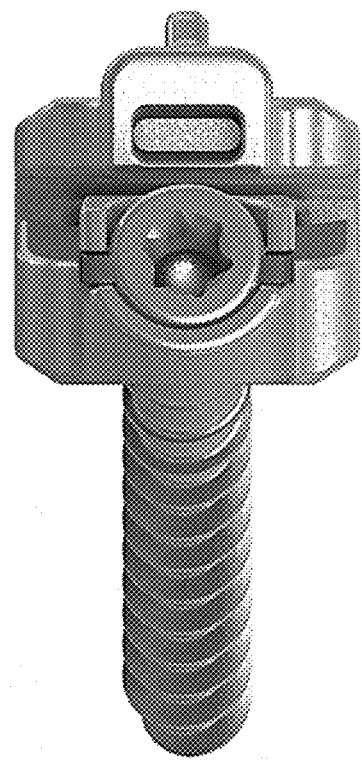

FIGS. 4A through 4D depict one exemplary lordotic correction that could be obtained using the teachings of the present invention. In this embodiment, a vertebral body 200 is imaged, and a surgical resection plan is proposed (indicated as the shaded triangle). FIG. 4B shows the vertebral body 200 after resection, and FIG. 4C depicts the new orientation of the vertebral body 200 after resection is complete, which could represent an increased lordotic curvature of the lumbar spine when accomplished at the lumbar level. FIG. 4D depicts the resulting correction to the functional spinal unit, wherein a negative 4 degree curvature was altered and stabilized to a positive 14 degree curvature using the techniques and implants described herein.

Referring now to FIGS. 5 through 9, in one embodiment, a prosthetic device 30 can be provided that allows for significant resection of a vertebral body and/or pedicle (including resection and/or preparation of only part of a pedicle) and associated spinal structures, while still preserving stability and/or motion in the spinal joint. The prosthetic device 30 can include an upper joint component 32 and a lower joint component 34. The upper joint component 32 desirably includes an articulation surface 36, which may be smooth, concave, and/or generally spherical in shape. The lower joint component 34 can include an articulation surface 38, which may be smooth, convex, and/or generally spherical in shape. As assembled, the articulation surface 36 may engage the articulation surface 38 to produce a ball-and-socket style anterior joint.

As defined herein, a "spherical" shaped surface could include any curved surface having a uniform radius of curvature and may refer to a spherical cap or a segment of a sphere. In various alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface The upper joint component 32 may further include bumpers or motion limiters 40, 42 which in this embodiment are depicted as recessed shoulders. The lower joint component 34 can also include bumpers or motion limiters 44, 46 which in this embodiment are upwardly protruding extensions, spaced apart from the articulation surface 38. As will be described in greater detail below, the pair of motion limiters 40, 44 and the pair of motion limiters 42, 46 may serve to constrain flexion/extension motion to a desirable range, preventing or limiting the dislocation of the joint formed by the articulation surfaces 36, 38. The motion limiters may be shaped to provide a greater or lesser range of flexion/extension motion. For example, a surface on the motion limiter 44 angled away from the articulation surface 38 may permit greater flexion motion than would a motion limiter surface parallel to an axis of the spine.

The upper joint component 32 may further include an outer contact surface 48 for interfacing with the vertebral endplate 18, and the lower joint component 34 may include an outer contact surface 50 for interfacing with the vertebral endplate 24.

The upper joint component 32 may further include an upper keel 52 extending from the outer contact surface 48 and comprising an elongated portion 53 and an elongated portion 54. The elongated portion 54 may be taller than the elongated portion 53 to provide the prosthetic device 30 with greater stability in the hard cortical bone of the outer wall of the vertebral body 14. In this embodiment, the raised keel portion 54 has a sharpened and undercut leading edge 56 to encourage aggressive cutting of a channel in the vertebral body 14 and endplate 18, which could help prevent the device 30 from skiving off the vertebral body 14. In this embodiment, the raised keel portion 54 is approximately one-third the length of the upper keel 52 and extends to the posterior edge of the upper joint component to provide additional stability. In alternative embodiments, the upper keel may be longer or shorter to achieve desired stability. If desired, the lower joint component 34 may include a lower keel 58 extending from the outer contact surface 50.

In various alternative embodiments, the width of the keel may vary. For example, the lower portion of the keel may be narrower than the taller portion of the keel. In other embodiments, the keel may taper or have an undulating wave form. In still another alternative, the keel may be perforated or porous to promote bone ingrowth.

The upper joint component 32 may further include a posterior tab 60 extending upward from the posterior edge of the outer contact surface 48. In this embodiment, the tab 60 may be generally perpendicular or slightly acutely angled relative to the contact surface 48. The tab 60 may be integrally formed with or otherwise abut the posterior end of the upper keel 52. As will be described in greater detail below, the posterior tab 60 may serve as a stop to prevent the device 30 from being inserted too far anteriorly into the intervertebral disc space. The position of the tab 60 may be monitored with fluoroscopy or other visualization methods during surgery to determine the progress of the implantation and to confirm when the device 30 has been completely implanted with the posterior tab 60 in contact with a posterior wall of the vertebral body 14. Because the position of the posterior tab 60 may be fixed relative to a center of rotation of the joint formed by articulation surfaces 36, 38, the location of the posterior tab 60 may serve as an indicator of the location of the center of rotation. After the surgeon has determined the desired location for the center of rotation, the upper joint component 32 may be selected so that as the posterior tab 60 is positioned against the posterior wall of the vertebral body 14, the center of rotation is moved into the desired predetermined location.

The prosthetic device 30 may further include a support or "bridge" component 62, which extends posteriorly from the lower joint component 34. As installed, the bridge component 62 will desirably further extend posteriorly from the intervertebral disc space between the vertebral bodies, with a lower surface that abuts and/or engages with at least a portion of the pedicle 25 to a distal end 64.

The distal end 64 of the bridge 62 may include a connection component 66, which in this embodiment is a passage for accepting a fastener 68. In this embodiment, the fastener 68 is a bone screw, however in alternative embodiments, fasteners such as nails, staples, or other mechanical or chemical fasteners may be suitable. The orientation of the connection component 66 desirably permits the fastener 68 to become inserted extrapedicularly, such that the screw travels a path obliquely angled or skewed away from a central axis defined through a pedicle. The fastener 68 may be threaded across a portion of the pedicle 25 and into the vertebral body 20. Extrapedicular fixation may be any fixation into the pedicle that does not follow a path down a central axis defined generally posterior-anterior through the pedicle. In this embodiment, the screw passes through a wall portion of the pedicle, whereby it may achieve strong cortical fixation. In all embodiments, the fasteners may be at least partially recessed so as not to interfere with articulations, soft tissues, and neural structures.

As installed, the bridge 62 and the fastener 68 may limit excessive movement of the device 30, particularly during flexion/extension motions. Additionally, the bridge 62 may distribute the loads on the lower vertebra V2, reducing any opportunity for subsidence of the lower joint component 34 into the vertebral body.

If desired, the connection component 66 may further include an optional locking clip 70, which in this embodiment is an elastically deformable C-shaped structure which holds the fastener 68 in place, resisting any backward disengagement of the fastener 68, particularly when the joint 12 is in motion. It is understood that in alternative embodiments, the locking clip may be a cap, a clamp, an adhesive, or other suitable mechanical or chemical systems for limiting movement of the fastener 68.

The size and shape of the joint components 32, 34 and the bridge component 62 may be limited by the constraints of a posterior surgical approach. For example, the anterior joint components 32, 34 may be configured to cover a maximum vertebral endplate area to dissipate loads and reduce subsidence while still fitting through the posterior surgical exposure, Kambin's triangle, and other neural elements. To achieve maximum surface coverage, the material of the anterior joint components 32, 34 may extend anteriorly from the articulation surfaces 36, 38, respectively. The width of the bridge component 62 may also be selected to desirably pass through Kambin's triangle and to co-exist with the neural elements, yet provide sufficient cross-sectional area to the pedicle structures for additional support.

In alternative embodiments, the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion. In still other alternative embodiments, the heights of the upper and lower joint components may increase or decrease along the length of the component to create a desired lordosis or kyphosis. The ability to modify the resulting angle between the upper and lower vertebral contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

For all of the embodiments described herein, the prosthetic device 30 may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the prosthetic device 30 may be formed of different materials thus permitting metal on metal, metal on ceramic, metal on polymer, ceramic on ceramic, ceramic on polymer, or polymer on polymer constructions.

In any one of the described embodiments, the bone contacting surfaces of the prosthetic device 30 including contact surfaces 48, 50; keels 52, 58; and bridge 62 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the prosthetic device 30 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The prosthetic device 30 may be installed between the vertebrae V1, V2 as will be described below. The prosthetic device 30 may be implanted into a patient using a posterior transforaminal approach similar to the known TLIF (transforaminal lumbar interbody fusion) or PLIF (posterior lumbar interbody fusion) procedures. PLIF style approaches are generally more medial and rely on more retraction of the traversing root and dura to access the vertebral disc space. The space between these structures is known as Kambin's triangle. TLIF approaches are typically more oblique, requiring less retraction of the exiting root, and less epidural bleeding with less retraction of the traversing structures. It is also possible to access the intervertebral space using a far lateral approach, above the position of the exiting nerve root and outside of Kambin's triangle. In some instances, it may be possible to access the intervertebral space via the far lateral without resecting the facets. Furthermore, a direct lateral approach through the psoas is known. This approach avoids the posterior neural elements completely. Embodiments of the current disclosure may adopt any of these common approaches or combinations thereof.

In various embodiments, some or all of the affected disc D1 and surrounding tissue may be removed via the foramina. The superior endplate of the vertebra may be milled, rasped, or otherwise resected to match the profile of the outer contact surface 50 of the lower joint component 34 to normalize stress distributions on the endplate 24, and/or to provide initial fixation prior to bone ingrowth. The preparation of the endplate 24 of vertebra V2 may result in a flattened surface or in surface contours such as pockets, grooves, or other contours that may match corresponding features on the outer contact surface 50. The inferior endplate of the vertebra may be similarly prepared to receive the upper joint component 32 to the extent allowed by the exiting nerve root and the dorsal root ganglia. In various embodiments, the natural facet joint and the corresponding articular processes 16, 22 can be rasped and/or prepared to accommodate and/or support an outer surface of the bridge component 62.

FIGS. 10 through 14 depict various views of one alternative embodiment of a prosthetic device constructed in accordance with various teaching of the present invention. In this embodiment, the prosthetic device 30*a* can include an upper joint component 32*a* and a lower joint component 34*a*, with the upper joint component 32*a* including an articulation surface 36*a*, and the lower joint component 34*a* including an articulation surface 38*a*. When assembled, the articulation surface 36*a* may engage the articulation surface 38*a* to produce a ball-and-socket style anterior joint.

In this embodiment, the upper joint component 32*a* can further include bumpers or motion limiters 40*a* and 42*a*, which in this embodiment are depicted as recessed shoulders. The lower joint component 34*a* can also include bumpers or motion limiters 44*a* and 46*a*, which in this embodiment are upwardly protruding extensions, spaced apart from the articulation surface 38*a*. In a manner similar to the previously described embodiments, the pair of motion limiters 40*a* and 44*a* and the pair of motion limiters 42*a* and 46*a* may serve to constrain flexion/extension motion to a desirable range, preventing or limiting the dislocation of the joint formed by the articulation surfaces 36*a* and 38*a*. The motion limiters may be shaped to provide a greater or lesser range of flexion/extension motion. For example, a surface on the motion limiter 44*a* angled away from the articulation surface 38*a* may permit greater flexion motion than would a motion limiter surface parallel to an axis of the spine.

The upper joint component 32*a* may further include an outer contact surface 48*a* for interfacing with a lower surface of the upper vertebral endplate, and the lower joint component 34*a* may include an outer contact surface 50*a* for interfacing with a upper surface of the lower vertebral endplate, the lower vertebral pedicle and/or other surfaces of the lower vertebral body.

The upper joint component 32*a* may further include an upper keel 300 extending from the outer contact surface 48*a* and comprising an elongated portion 310. The elongated portion 310 will desirably extend upward from the outer contact surface 48*a*, to provide the prosthetic device 30*a* with greater stability in the upper vertebral body. In this embodiment, the upper keel portion 300 may have a sharpened and/or undercut leading edge, if desired. In alternative embodiments, the upper keel may be longer or shorter to achieve desired stability. If desired, the lower joint component 34 may include a lower keel 58*a* extending from the outer contact surface 50*a*.

In various alternative embodiments, the width of the keel may vary. For example, the lower portion of the keel may be narrower than the taller portion of the keel. In other embodiments, the keel may taper or have an undulating wave form. In still another alternative, the keel may be perforated or porous to promote bone ingrowth.

In various embodiments, the upper joint component 32*a* may further include a posterior tab 60*a* extending upward from the posterior edge of the outer contact surface 48*a*. In this embodiment, the tab 60*a* may be generally perpendicular or slightly acutely angled relative to the contact surface 48*a*. The tab 60*a* may be integrally formed with or otherwise abut the posterior end of the upper keel 300. In a manner similar to previously described embodiments, the posterior tab 60*a* may serve as a stop to prevent the device 30*a* from being inserted too far anteriorly into the intervertebral disc space. The position of the tab 60*a* may be monitored with fluoroscopy or other visualization methods during surgery to determine the progress of the implantation and to confirm when the device 30*a* has been completely implanted with the posterior tab 60*a* in contact with a posterior wall of the vertebral body. Because the position of the posterior tab 60*a* may be fixed relative to a center of rotation of the joint formed by articulation surfaces 36*a* and 38*a*, the location of the posterior tab 60*a* may serve as an indicator of the location of the center of rotation. After the surgeon has determined the desired location for the center of rotation, the upper joint component 32*a* may be selected so that as the posterior tab 60*a* is positioned against the posterior wall of the vertebral body, the center of rotation is moved into the desired predetermined location.

The prosthetic device 30*a* will desirably further include a support or "bridge" component 62*a*, which extends posteriorly from the lower joint component 34*a*. As installed, the bridge component 62*a* will desirably further extend posteriorly from the intervertebral disc space between the vertebral bodies, with a lower surface that abuts and/or engages with at least a portion of a pedicle (and/or other vertebral structures) to a distal end 64*a*.

The distal end 64*a* of the bridge 62*a* may include a connection component 66*a*, which in this embodiment is a passage for accepting a fastener 68*a*. In this embodiment, the fastener 68*a* is a bone screw, however in alternative embodiments, fasteners such as nails, staples, or other mechanical or chemical fasteners may be suitable. The orientation of the connection component 66*a* desirably permits the fastener 68*a* to become inserted extrapedicularly, such that the screw travels a path obliquely angled or skewed away from a central axis defined through a pedicle. The fastener 68*a* may be threaded across a portion of the pedicle and into the vertebral body. Extrapedicular fixation may be any fixation into the pedicle that does not follow a path down a central axis defined generally posterior-anterior through the pedicle. In this embodiment, the screw may pass through a wall portion of the pedicle and/or vertebral body, whereby it may achieve strong cortical fixation. In all embodiments, the fasteners may be at least partially recessed so as not to interfere with articulations, soft tissues, and neural structures.

As previously noted, alternative embodiments of the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion and/or spinal alignment. In still other alternative embodiments, the heights of the upper and lower joint components may increase or decrease along the length of the component to create a desired lordosis or kyphosis and/or accommodate a desired surgical resection and/or correction. The ability to modify the resulting angle between the upper and lower vertebral contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

Exemplary Surgical Procedure

According to at least one embodiment, a first surgical incision for providing access via a bilateral approach is made in the patient's back, and a decompression of the posterior vertebral elements on a first posterior side of the spinal motion unit (i.e., removal of portions of the upper and/or lower facets on the medial side, for example) or other standard bilateral decompression can be accomplished to provide access to the intervertebral disc space. A discectomy can then be accomplished through the access, and a distractor/trial can be placed between the vertebral bodies, with the overlying skin and tissues allowed to relax. A second surgical incision is made to provide access to the opposing (i.e., lateral) side of the spinal motion unit, and then a similar decompression and discectomy can be accomplished through the lateral access.

Figure 18:
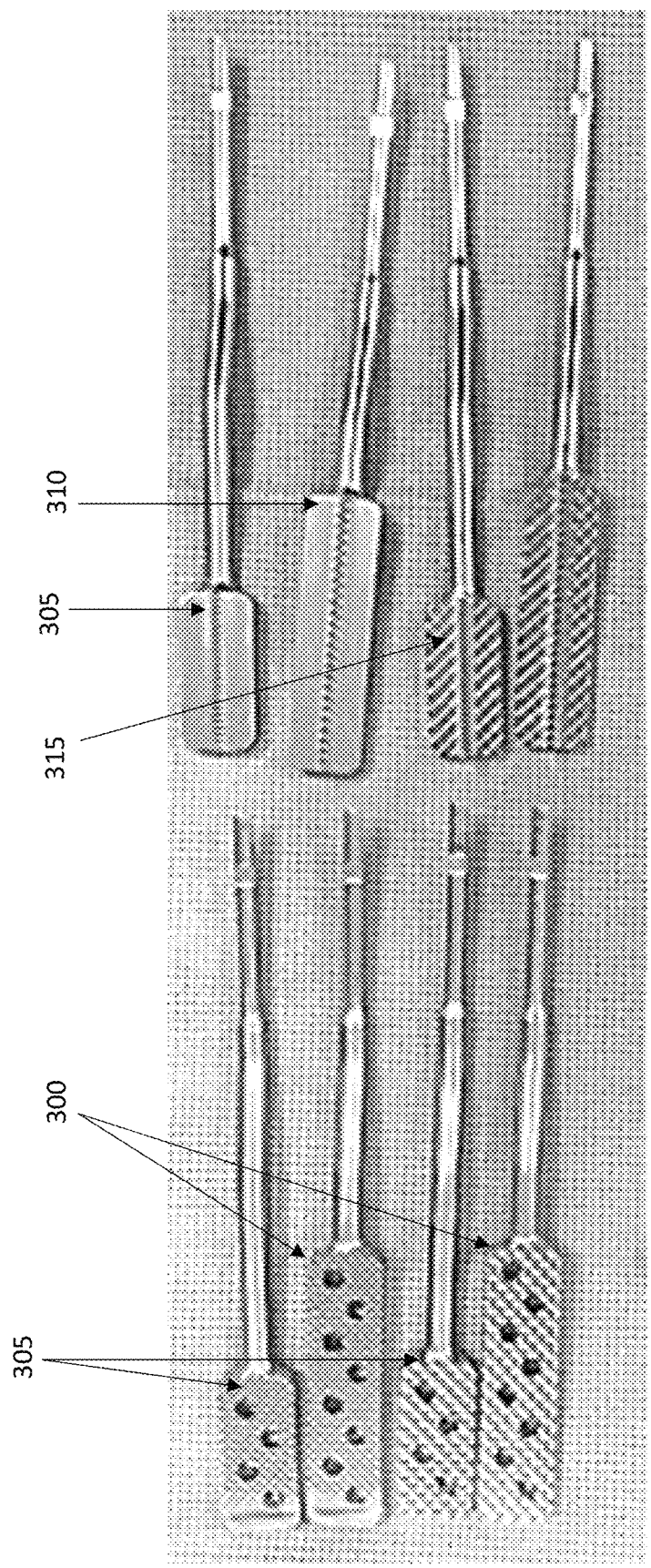
FIG. 18 depicts a top plan view of various rasps and alignment tools for use in preparing spinal anatomy.

The surgeon can then rasp, resect and/or otherwise remove portions of the vertebral body, the pedicle and/or other posterior structures of the vertebral body, including portions of the upper endplate of the lower vertebral body, in accordance with the preoperative surgical plan. In various embodiments, a long flat rasp 300 (see FIG. 18) can be utilized to remove and prepare the upper surface of the lower vertebral body and pedicle, and a short rasp 305 can be similarly used on the lower endplate of the upper vertebral body, such as to flatten or otherwise prepare the top of the disc space. Once the upper surface of the lower vertebral body has been prepared using the flat rasp, a long keel rasp 310 can be utilized to prepare a keel slot or similar feature in the vertebral body and/or pedicle. A short rasp with a non-cutting index 315 can then be utilized to mark the top keel and align it with the cut along the pedicle, and then the top keel groove can be formed in the upper vertebral body using the short keeled rasp 305.

Once one side of the vertebral body and disc space have been prepared in this fashion, a spacer or trial may be placed into the disc space to ensure the vertebral bodies have been properly prepared, that a desired angular correction has been established, and/or that a desired tension of the lateral annulus will be achieved once the final implant has been emplaced. If the trial/spacer appears to properly fit, then the trial/spacer can be removed and replaced with the assembled implant. Once the assembled implant is in a desired position, an anchoring screw or other anchoring device can be inserted through the connection component and secured to the lower vertebral body.

In various embodiments, the long flat rasp or other surgical tool(s) could be attached to a surgical guidance system, allowing a surgeon to view the predicted and/or actual path of the rasp/tool on the targeted anatomy. Various additional steps of the procedure as outlined could be accomplished using a surgical guidance system, with at least one benefit of surgical guidance potentially reducing radiation exposure to the patient and/or operative room personnel while enhancing the accuracy and/or fidelity of the anatomical preparation by matching the preoperative plan with the intraoperative execution in three dimensions.

In other alternative embodiments, the various steps described herein could be accomplished with the aid of a surgical robot, with or without surgical navigation. In one embodiment, the surgical robot could provide haptic feedback to the surgeon, which might desirably notify the surgeon of approaching soft tissues and/or other surgical boundaries. In another embodiment, the robot could provide rigid limits for surgeon activity (i.e., to prevent cutting into delicate tissues, for example). In a third embodiment, the surgical robot could complete surgical steps autonomously (i.e., with or without surgeon intervention). The employment of surgical robots as outlined could potentially reduce radiation exposure to the patient and/or operative room personnel while enhancing the accuracy and/or fidelity of the anatomical preparation by matching the preoperative plan with the intraoperative execution in three dimensions.

Once one side of the vertebral body has been treated in the previous manner, the same approach can be repeated on the other side of the vertebral body, including trialing and placement of the final implant. One particularly advantageous feature of the present invention is that the disclosed technique allows a surgeon to trial and "balance" the medial and lateral annulus for proper tension/laxity, in a manner similar to balancing of a knee implant. Such balancing, which is not currently possible using existing devices and surgical techniques, can significantly improve the stability and performance of the spinal implant, and can also contribute greatly to device function and durability, as well as significantly reduced patient pain and/or recovery time, leading to increased patient satisfaction with this procedure.

Figure 19:
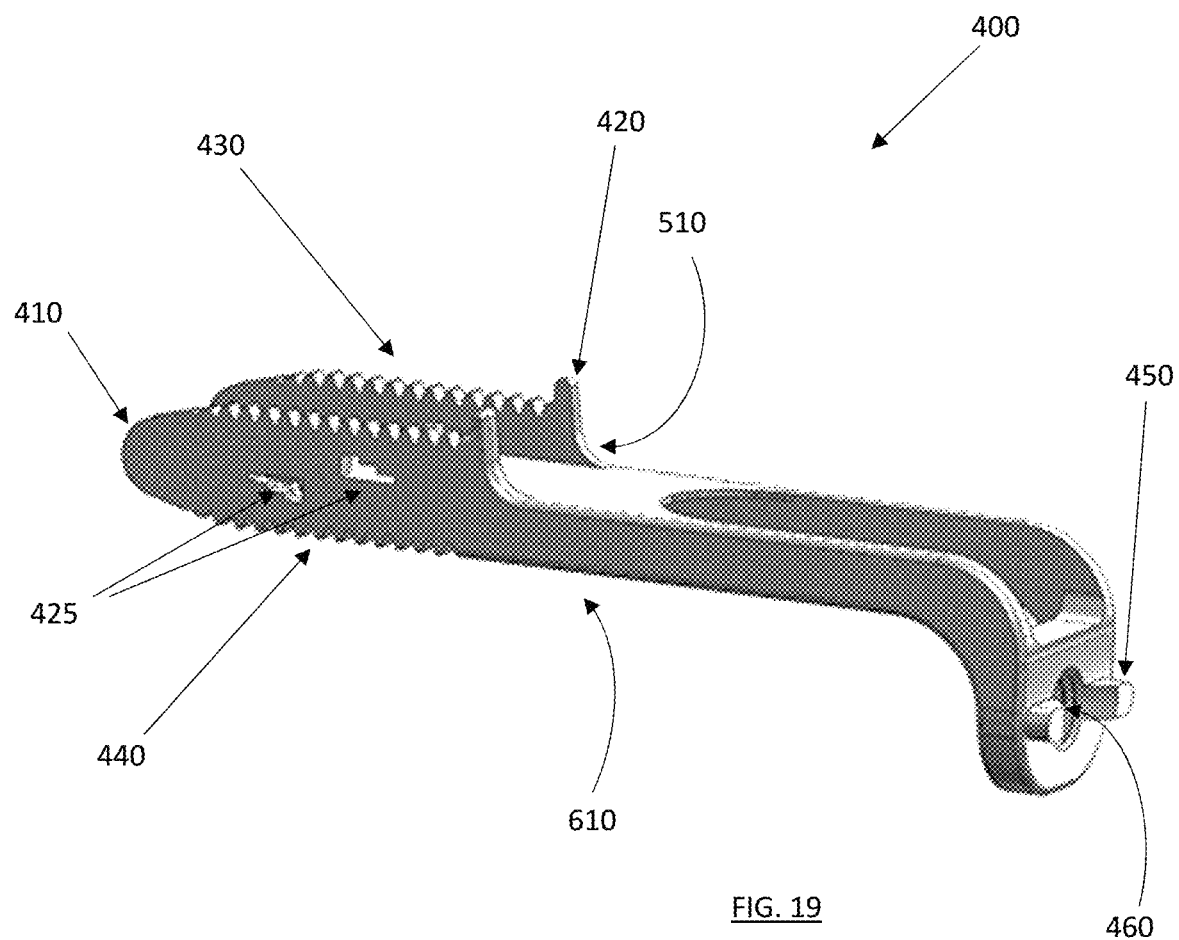
FIG. 19 depicts a perspective view of one exemplary embodiment of a trial and rasp guide.

FIG. 19 depicts one exemplary embodiment of a trial and rasp guide 400, which could be used with various embodiments of the present invention. The guide 400 can be provided in kit of guides of differing heights, including kits having one or more guides with heights of 8 mm, 9 mm, 10 mm, 11 mm, 12 mm, 13 mm, 14 mm and/or the like. In this embodiment, the guide 400 can include a bullet nose 410 which gradually increases to the full height of the guide (allowing for insertion of the guide into spaces that are somewhat more narrow than the full guide height), a depth stop 420, one or more depth indicator windows 425, an upper textured surface 430 (which could be a toothed pattern or other pattern), a lower texture surface 440, an insertion instrument attachment point 450 and an anchor receiver 460. Desirably, the anchor receiver 460 will be sized and configured to accept a pedicle screw or other anchoring device therein.

Figure 20A:
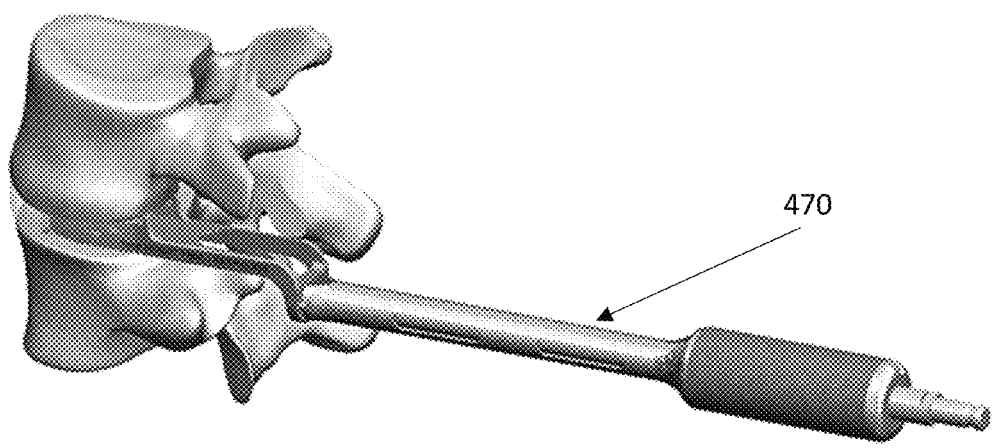
FIGS. 20A through 20F and 21A through 21C depict exemplary steps for using the guide of FIG. 19 in preparing a functional spinal unit for an implant.
Figure 20B:
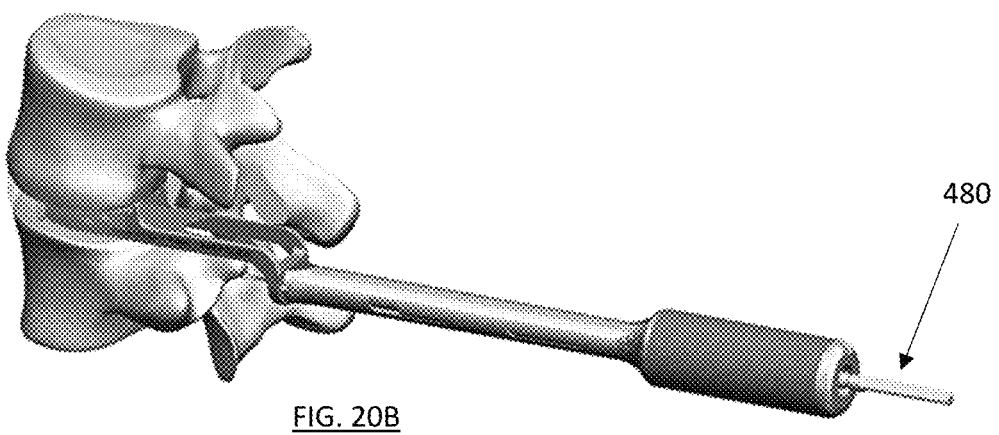
Figure 20C:
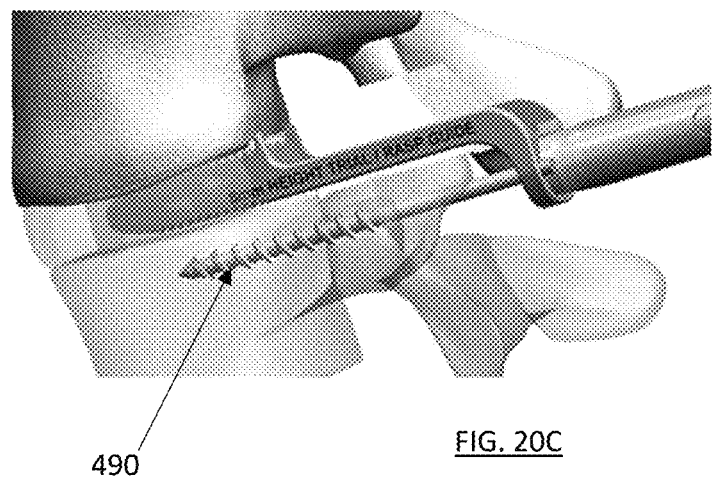
Figure 20D:
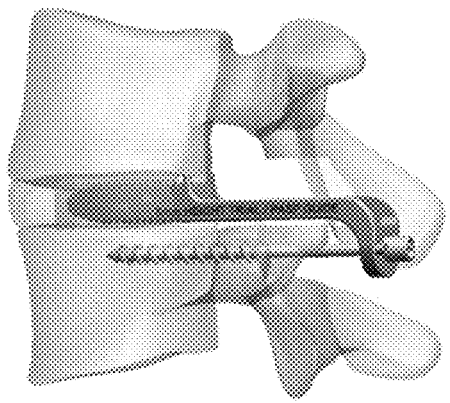
Figure 20E:
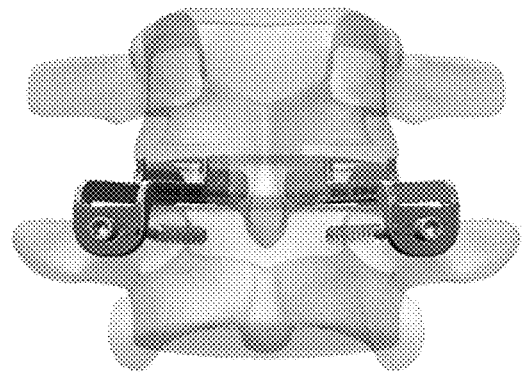
Figure 20F:
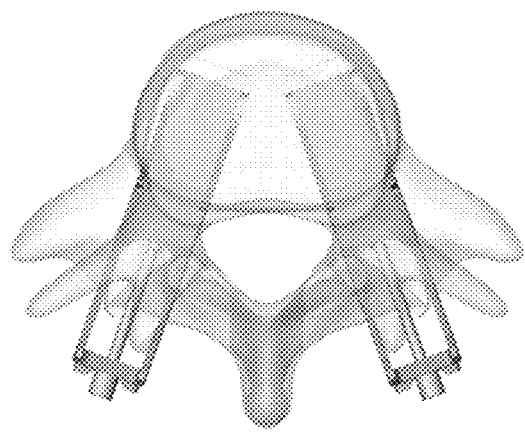

In use, the guide 400 can be attached to a placement tool 470 (see FIG. 20A) and inserted into one side of a functional spinal unit after the posterior elements have been removed, and the disc space initially prepared. The positioning and/or placement of the guide 400 will desirably be monitored and/or controlled using fluoroscopic or other guidance, and then a threaded inner rod 480 (see FIG. 20B) of the placement tool 470 can be removed and a pilot anchor hole (not shown) can be drilled into the vertebral body. A pedicle pin 490 or other anchoring device (see FIG. 20C) can then be placed into the vertebral body through the placement tool and the tool 470 can be removed. A second guide 405 can then be placed into the other side of the functional spinal unit, and the guide placement and orientation can be verified using fluoroscopy or other imaging techniques, as well as via direct visualization (See FIGS. 20D through 20F).

Figure 21A:
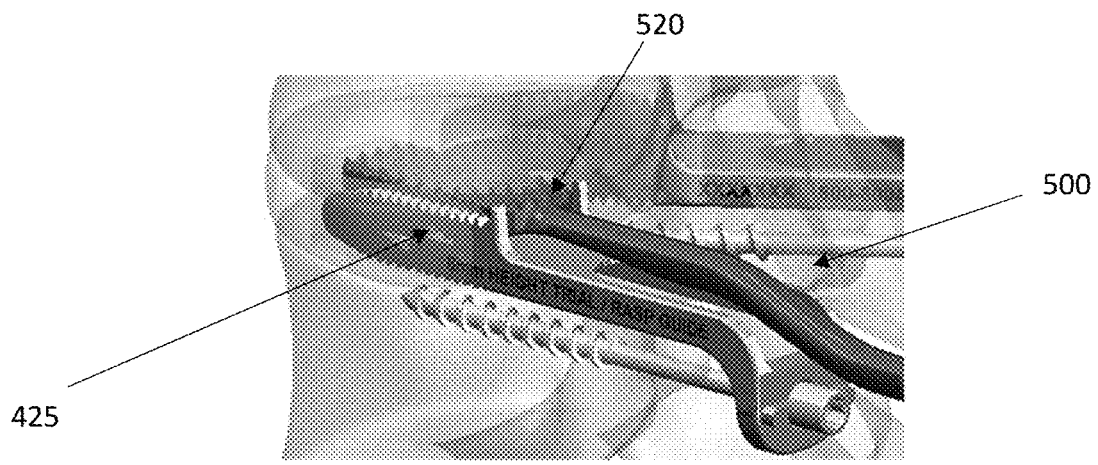
Figure 21B:
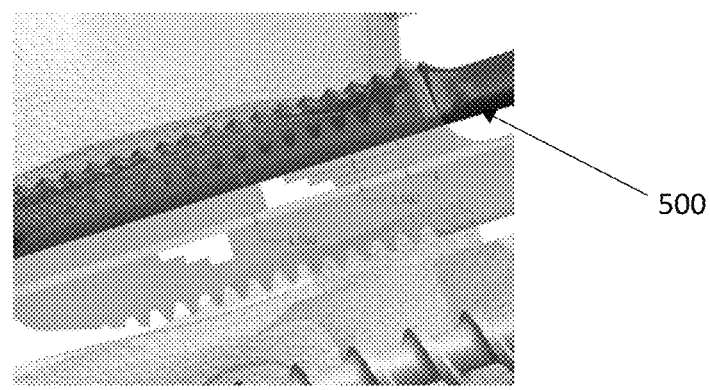

A rasp 500 can then be inserted into an upper channel 510 of the guide 400 (see FIG. 21A) to begin superior endplate bone preparation, and the rasp anterior depth can be monitored and/or limited by aligning a proximal end 520 of the rasp with the posterior vertebral wall of the upper vertebral body. The depth of rasping into the upper endplate can be monitored and/or controlled using the depth indicator windows 425, which can be monitored fluoroscopically. In the exemplary embodiment, each step of a cutout in the depth indicator windows 425 can represent 0.5 mm increments, although other depth increments may be preferred. The depth of the rasp is desirably indicated by the smooth (i.e., non-cutting) side of the rasp which aligns with steps in the depth indicator window 425 (see FIG. 21B). When a desired shape and extent of upper endplate preparation is achieved, the rasp 500 can then be removed.

Figure 21C:
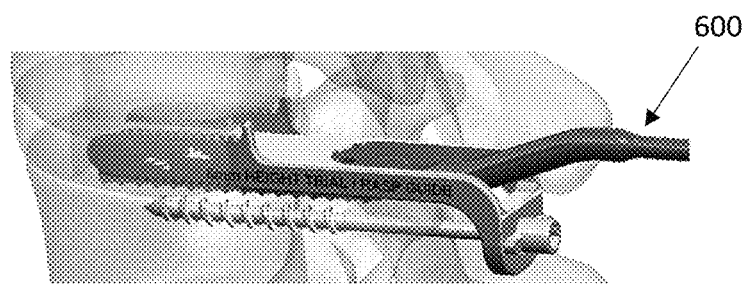

A long rasp 600 can then be inserted into a lower channel 610 of the guide 400, with the rasp used to cut and prepare the lower vertebral endplate, pedicle and/or other vertebral structures (see FIG. 21C) in a manner similar to the upper endplate, including the use of the depth stop to monitor rasping depth. Once the lower endplate preparation is complete, similar steps can be taken to prepare the vertebral bodies on the contralateral side of the spinal motion unit, and then placement of the spinal prostheses could be effectuated.

Spinal Fusion Implants

Figure 22:
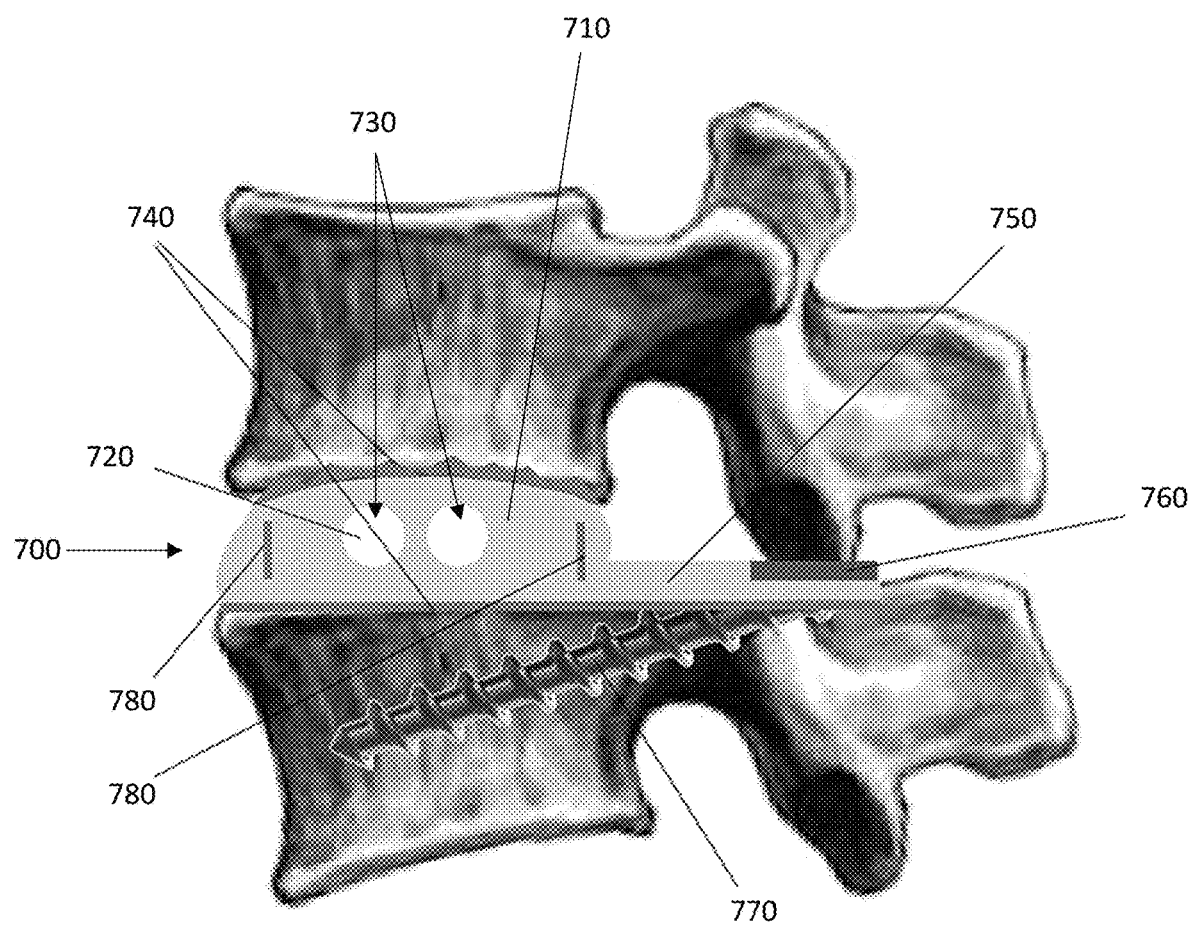
FIG. 22 depicts a side view of one embodiment of a fusion implant for use with various teachings of the present invention.

In various embodiments, a spinal fusion device may be implanted into a functional spinal unit for a variety of reasons, including to restore stability to a significantly degraded and/or unstable spinal level. FIG. 22 depicts one exemplary embodiment of a fusion implant 700 that could be implanted bilaterally in a manner similar to the embodiments previously described. In this embodiment, the fusion implant 700 includes a central body 710 having an open graft window 720 with side ports 730 for graft cell placement, ingrowth or on-growth surfaces 740 for bony integration with the adjacent vertebral surfaces, a bridge or tail 750 for integrating with the prepared pedicle surfaces (i.e., to prevent subsidence and/or to cross the foramen) and a screw or anchor retention feature 760 for accommodating an anchoring screw 770. In addition, the implant 700 could desirably include radiopaque markers 780 or other features to allow the position and/or orientation of the implant 700 to be monitored in a non-invasive manner after surgery.

Figure 23:
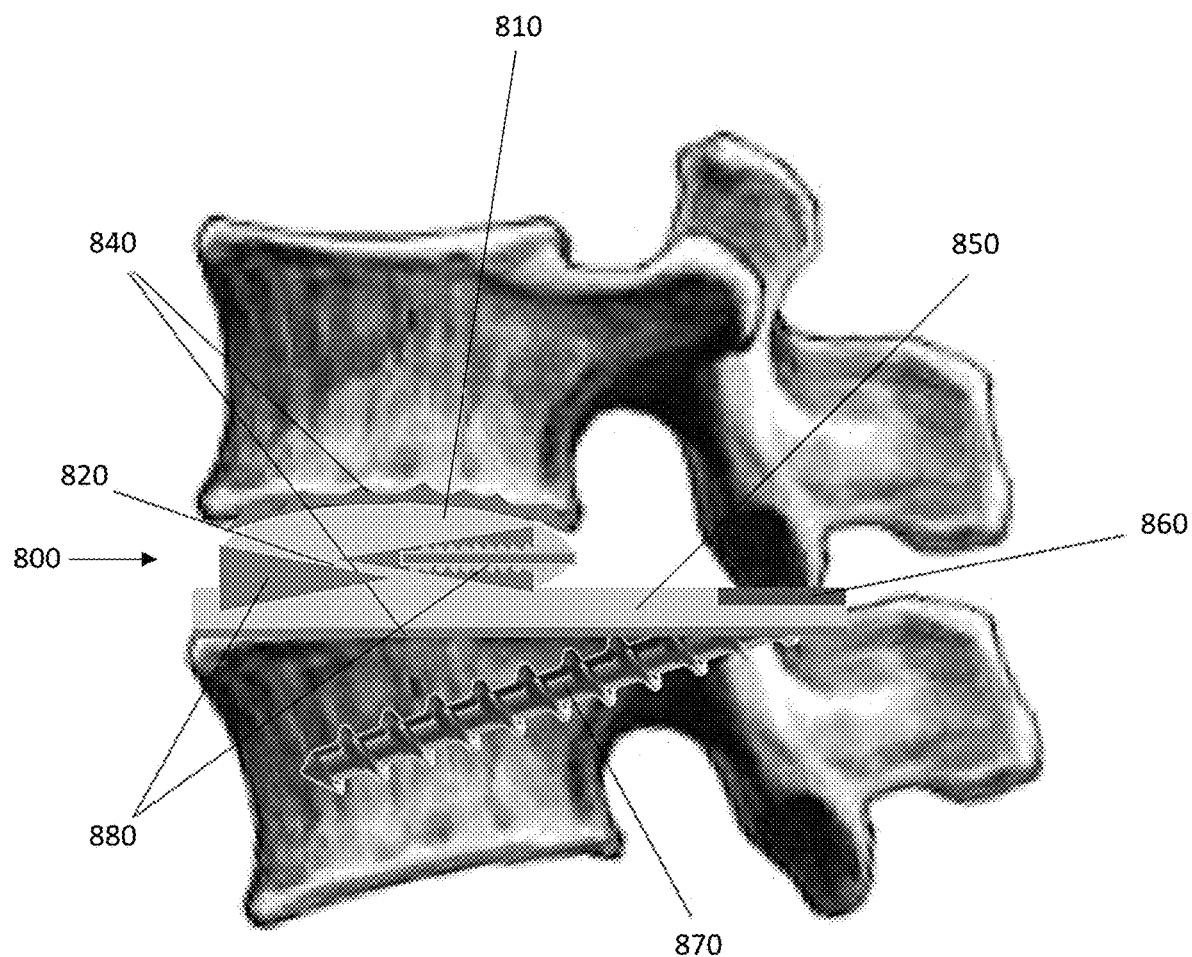
FIG. 23 depicts a side view of one embodiment of an expandable fusion implant for use with various teachings of the present invention.

FIG. 23 depicts another alternative embodiment of a fusion implant 800, which desirably allows for expansion and/or modification of the implant height during surgery. In this embodiment, the implant 800 includes a central body 810 having an optional open graft window 820 with side ports (not shown) for graft cell placement, ingrowth or on-growth surfaces 840 for bony integration with the adjacent vertebral surfaces (which could include milled and/or freehand techniques—i.e., anatomical fit), a bridge or tail 850 for integrating with the prepared pedicle surfaces (i.e., to prevent subsidence and/or to cross the foramen) and a screw or anchor retention feature 860 for accommodating an anchoring screw 870. In addition, the implant 800 desirably includes wedges of other expansion features 880, which could include vertical-only expansion, sagittal expansion and/or some combination of vertical/sagittal expansion.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A surgical method for creating a desired lordosis or kyphosis between an upper vertebrae and lower vertebrae during a spinal fusion procedure, comprising:
   removing at least a portion of a natural intervertebral disc from between the upper and lower vertebrae to create a disc space;
   removing at least a portion of a natural pedicle, a posterior rim portion and an upper endplate portion of the lower vertebrae to create a resected lower vertebral surface and a resected pedicle surface, at least a portion of the resected lower vertebral surface comprising a cancellous bone of the lower vertebrae;
   inserting a first arthroplasty device at least partially into the disc space, the first arthroplasty device including:
      an upper surface configured to engage with a lower endplate surface of the upper vertebrae;
      a lower surface configured to engage with the resected lower vertebral surface, the upper surface fixed to the lower surface to inhibit relative motion therebetween; and
      a bridge portion having a bridge surface for engaging with the resected pedicle surface and a connection component for engaging with a bone fastener, the bridge portion extending through the removed posterior rim portion of the lower vertebrae;
   wherein, when the first arthroplasty device is positioned at least partially within the disc space and attached to the lower vertebrae, the first arthroplasty device inhibits relative motion between the upper and lower vertebrae.

2. The surgical method of claim 1, further comprising inserting a second arthroplasty device at least partially into the disc space, the second arthroplasty device being spaced apart from the first arthroplasty device.

3. The surgical method of claim 1, further comprising inserting a second arthroplasty device at least partially into the disc space, the second arthroplasty device being spaced apart laterally from the first arthroplasty device.

4. The surgical method of claim 1, wherein the first arthroplasty device includes a graft chamber for graft placement during the spinal fusion procedure.

5. The surgical method of claim 1, wherein the bone fastener comprises a bone screw which extends through a cortical wall of the natural pedicle.

6. The surgical method of claim 1, wherein the bone fastener comprises a bone screw which extends through resected pedicle surface of the natural pedicle.

7. The surgical method of claim 1, wherein the first arthroplasty device include at least one radiopaque marker.

8. The surgical method of claim 1, wherein the first arthroplasty device comprises a central body having the upper and lower surfaces integrally formed therein.

9. A surgical method for creating a desired lordosis or kyphosis between an upper vertebrae and lower vertebrae during a spinal fusion procedure, comprising:
- removing at least a portion of a natural intervertebral disc from between the upper and lower vertebrae to create a disc space;
- removing at least a portion of a natural pedicle, a posterior rim portion and an upper endplate portion of the lower vertebrae to create a resected lower vertebral surface and a resected pedicle surface, at least a portion of the resected lower vertebral surface comprising a cancellous bone of the lower vertebrae;
- inserting a first arthroplasty device at least partially into the disc space, the first arthroplasty device including:
  - a central body having an upper surface configured to engage with a lower endplate surface of the upper vertebrae and a lower surface configured to engage with the resected lower vertebral surface, the central body including a adjustment mechanism to permit the upper and lower surfaces to be selectively moved from a first relative spacing to a second relative spacing, the first relative spacing being a different implant dimension than the second relative spacing; and
  - a bridge portion having a bridge surface for engaging with the resected pedicle surface and a connection component for engaging with a bone fastener, the bridge portion extending through the removed posterior rim portion of the lower vertebrae;
- wherein, when the first arthroplasty device is positioned at least partially within the disc space and attached to the lower vertebrae, the first arthroplasty device inhibits relative motion between the upper and lower vertebrae.

10. The surgical method of claim 9, wherein the first relative spacing comprises a first implant height between the upper and lower surfaces and the second relative spacing comprises a second implant height between the upper and lower surfaces.

11. The surgical method of claim 9, wherein the first relative spacing comprises a first sagittal length between the upper and lower surfaces and the second relative spacing comprises a second sagittal length between the upper and lower surfaces.

12. The surgical method of claim 9, further comprising inserting a second arthroplasty device at least partially into the disc space, the second arthroplasty device being spaced apart from the first arthroplasty device.

13. The surgical method of claim 9, further comprising inserting a second arthroplasty device at least partially into the disc space, the second arthroplasty device being spaced apart laterally from the first arthroplasty device.

14. The surgical method of claim 9, wherein the first arthroplasty device includes a graft chamber for graft placement during the spinal fusion procedure.

15. The surgical method of claim 9, wherein the bone fastener comprises a bone screw.

16. The surgical method of claim 9, wherein the bone fastener comprises a bone screw which extends through resected pedicle surface of the natural pedicle.

17. The surgical method of claim 9, wherein the first arthroplasty device include at least one radiopaque marker.

18. The surgical method of claim 9, wherein the first arthroplasty device comprises a central body having the upper and lower surfaces integrally formed therein.

19. A surgical method for creating a desired lordosis or kyphosis between an upper vertebrae and lower vertebrae during a spinal fusion procedure, comprising:
- removing at least a portion of a natural intervertebral disc from between the upper and lower vertebrae to create a disc space;
- removing at least a portion of a first natural pedicle, a first posterior rim portion and a first upper endplate portion of the lower vertebrae to create a first resected lower vertebral surface and a first resected pedicle surface, at least a portion of the first resected lower vertebral surface comprising a first cancellous bone portion of the lower vertebrae;
- inserting a first arthroplasty device at least partially into the disc space, the first arthroplasty device including:
  - a first central body having a first upper surface configured to engage with a first lower endplate surface of the upper vertebrae and a first lower surface configured to engage with the first resected lower vertebral surface, and a first bridge portion connected to the first central body, the first bridge portion having a first bridge surface for engaging with the first resected pedicle surface and a first connection component for engaging with a first bone fastener, the first bridge portion extending through the removed first posterior rim portion of the lower vertebrae;
- removing at least a portion of a second natural pedicle, a second posterior rim portion and a second upper endplate portion of the lower vertebrae to create a second resected lower vertebral surface and a second resected pedicle surface, at least a portion of the second resected lower vertebral surface comprising a second cancellous bone portion of the lower vertebrae;
- inserting a second arthroplasty device at least partially into the disc space, the second arthroplasty device including:
  - a second central body having a second upper surface configured to engage with a second lower endplate surface of the upper vertebrae and a second lower surface configured to engage with the second resected lower vertebral surface, and a second bridge portion having a second bridge surface for engaging with the second resected pedicle surface and a second connection component for engaging with a second bone fastener, the second bridge portion extending through the removed second posterior rim portion of the lower vertebrae;
- wherein, when the first and second arthroplasty devices are positioned at least partially within the disc space and attached to the lower vertebrae, relative motion between the upper and lower vertebrae is inhibited.

20. The surgical method of claim 19, wherein the second arthroplasty device is spaced apart from the first arthroplasty device.

* * * * *